United States Patent [19]

Nose et al.

[11] Patent Number: 5,742,386
[45] Date of Patent: Apr. 21, 1998

[54] APPARATUS FOR DETECTING FOREIGN MATTER ON A SUBSTRATE, AND AN EXPOSURE APPARATUS INCLUDING THE SAME

[75] Inventors: Noriyuki Nose, Atsuigi; Minoru Yoshii, Tokyo; Kyoichi Miyazaki, Utsunomiya; Toshihiko Tsuji, Utsunomiya; Seiji Takeuchi, Utsunomiya, all of Japan

[73] Assignee: Canon Kabushiki Kaisha, Tokyo, Japan

[21] Appl. No.: 799,879

[22] Filed: Feb. 13, 1997

Related U.S. Application Data

[63] Continuation of Ser. No. 711,309, Sep. 3, 1996, abandoned, which is a continuation of Ser. No. 281,181, Jul. 27, 1994, abandoned.

[30] Foreign Application Priority Data

Jul. 30, 1993 [JP] Japan ................................ 5-208367
Apr. 25, 1994 [JP] Japan ................................ 6-110436

[51] Int. Cl.[6] .................................................. G01N 21/00
[52] U.S. Cl. ....................................... 356/237; 356/239
[58] Field of Search ................................ 356/287, 359, 356/360

Primary Examiner—Frank G. Font
Assistant Examiner—Robert Kim
Attorney, Agent, or Firm—Fitzpatrick, Cella, Harper & Scinto

[57] ABSTRACT

An apparatus for detecting foreign matter on a substrate includes an optical system for projecting a light beam onto a pellicle and a pattern surface, a first detector for detecting scattered light from foreign matter on the pattern surface, a second detector for detecting information relating to the reflectivity or the transmittance of the pellicle by detecting a light beam reflected by the pellicle, and a correction unit for correcting an output signal from the first detector using an output signal from the second detector.

10 Claims, 8 Drawing Sheets

APPARATUS FOR DETECTING FOREIGN MATTER ON A SUBSTRATE, AND AN EXPOSURE APPARATUS INCLUDING THE SAME

This application is a continuation of prior application Ser. No. 08/711,309, filed Sep. 3, 1996, which application is a continuation of prior application Ser. No. 08/281,181, filed Jul. 27, 1994.

BACKGROUND OF THE INVENTION

1. Field of the Invention

This invention relates to an apparatus for detecting foreign matter on a substrate, and more particularly, to a foreign-matter inspection apparatus in which when a protective pellicle is mounted on a substrate, such as a reticle, a photomask or the like, having thereon a circuit pattern used in a semiconductor-device manufacturing apparatus, foreign matter, such as opaque dust particles or the like, adhering to the surface of the substrate can be very precisely detected.

2. Description of the Related Art

In general, in the process of manufacturing IC's (integrated circuits) or other semiconductor devices, devices are manufactured by transferring a circuit pattern for exposure formed on a substrate, such as a reticle, a photomask or the like, onto the surface of a wafer, on which a resist has been coated, using a semiconductor printing apparatus (a stepper or a mask aligner).

At that time, if foreign matter, such as dust particles or the like, is present on the surface of the substrate, the foreign matter is simultaneously transferred, thereby causing a decrease in the production yield in the manufacture of IC's. Accordingly, it is indispensable to detect the presence of foreign matter on a substrate in the IC manufacturing process, and various kinds of inspection apparatuses have been proposed.

In general, in order to prevent foreign matter present, for example, on the surface of a photomask, used in the phototoetching process in the manufacture of semiconductor devices, from being transferred during projection and exposure to cause a pattern failure, a pellicle is mounted above the surface.

FIG. 6 is a schematic diagram illustrating a photomask on which a pellicle is mounted. In FIG. 6, a pellicle 50 comprises a tranparent thin film made of nitrocellulose or the like. The pellicle 50 is fixed to a pellicle frame 51, made of an aluminum alloy or the like, in order to cover a pattern portion (not shown) on a photomask 52. Since incident light passes through the pellicle 50 when inspecting foreign matter adhering to the surface of the photomask 52, the transmittance and the reflectivity of the light change depending on the thickness of the pellicle 50.

FIG. 5 is a schematic diagram illustrating a principal portion of a conventional foreign-matter detecting apparatus for detecting foreign matter, such as dust particles or the like, adhering to the surface of the photomask 52 on which a circuit pattern is formed.

In FIG. 5, a light beam 49 emitted from a laser light source (not shown) is projected onto the surface of the photomask 52 to be measured, and the surface is scanned with the light beam 49 in a direction perpendicular to the plane of FIG. 5 using a scanning optical system, comprising a polygonal mirror and the like.

Scattered light 48 from foreign matter 44 on the surface of the photomask 52 is detected by a photodetector 46 via a condensing optical system 47. Utilizing the relationship between the size of the foreign matter 44 and the amount of scattered light 48, the foreign matter 44 is discriminated, for example, as foreign matter having a size less than 1.0 μm, foreign matter having a size of 1.0 μm 2.0 μm, and the like.

In FIG. 5, the scanning direction of the beam 49 is the x-axis direction. The entire surface of the photomask 52 is scanned by moving a stage (not shown), on which the photomask 52 is mounted, in the z-axis direction, whereby foreign matter on the surface of the photomask 52 is inspected.

At that time, a portion of the light beam 49 projected onto the surface of the photomask 52 is converted into scattered light from the foreign matter 44 and scattered light from the IC pattern on the photomask 52, which are detected by the photodetector 46. In order to increase the scattering ratio of the two kinds of scattered light, i.e., the so-called S/N ratio, polarization characteristics are utilized.

However, the foreign-matter inspection apparatus shown in FIG. 5 has the following problems.

(1-1) The light beam 49 projected onto the photomask 52 is reflected by the pellicle 50, whereby the amount of light projected onto the IC pattern on the photomask 52 is reduced. The amount of the scattered light 48 from the foreign matter 44 also changes (is reduced).

In general, in the photomask 52 having the pellicle 50, the transmittance for the laser light beam 49 changes when the thickness of the pellicle 50 changes, whereby the amount of light projected onto the IC pattern on the photomask 52 changes. The amount of the scattered light 48 from the foreign matter 44 also changes. Accordingly, an error is produced in the detected size of the foreign matter 44.

(1-2) Variations are produced in the thickness of the pellicle 50 mounted on the photomask 52 due to different production lots, production control tolerances for the thickness, and the like.

Particularly when the incident light beam 49 comprises an S-polarized light beam, the reflection loss by the pellicle 50 is large, and therefore, the amount of detected light greatly depends on the thickness of the pellicle 50. Accordingly, it is difficult to precisely detect the size of the foreign matter 44.

SUMMARY OF THE INVENTION

It is an object of the present invention to provide an apparatus for detecting foreign matter on a substrate in which by monitoring the transmittance or the reflectivity of a pellicle, and correcting the amount of light projected onto the surface of a photomask based on the monitored value, foreign matter, such as dust particles or the like, adhering to the surface of the photomask, can be very precisely detected.

According to one aspect, the present invention which achieves the above-described object relates to an apparatus for detecting foreign matter on a substrate, comprising optical means for projecting a light beam onto a first surface and a second surface, a first detector for detecting scattered light from foreign matter on the second surface, a second detector for detecting information relating to the reflectivity or the transmittance of the first surface using the light beam reflected by the first surface, and correction means for correcting an output signal from the first detector using an output signal from the second detector.

According to another aspect, the present invention which achieves the above-described object relates to an apparatus for detecting foreign matter on a substrate, comprising optical means for projecting a light beam onto a first surface and a second surface, a first detector for detecting scattered light from foreign matter on the second surface, means for projecting the light beam reflected by the first surface again onto the first surface, a second detector for detecting the light beam reflected again by the first surface, and correction means for correcting an output signal from the first detector using an output signal from the second detector.

According to still another aspect, the present invention which achieves the above-described object relates to an exposure apparatus comprising an inspection apparatus for inspecting foreign matter on a mask, which includes a pellicle and a pattern surface, and exposure means for performing exposure using the mask. The inspection apparatus comprises optical means for projecting a light beam onto the pellicle and the pattern surface, a first detector for detecting scattered light from foreign matter on the pattern surface, a second detector for detecting information relating to the reflectivity or the transmittance of the pellicle using the light beam reflected by the pellicle, and correction means for correcting an output signal from the first detector using an output signal from the second detector.

According to yet another aspect, the present invention which achieves the above-described object relates to an exposure apparatus comprising an inspection apparatus for inspecting foreign matter on a mask, which includes a pellicle and a pattern surface, and exposure means for performing exposure using the mask. The inspection apparatus comprises optical means for projecting a light beam onto the pellicle and the pattern surface, a first detector for detecting scattered light from foreign matter on the pattern surface, means for projecting the light beam reflected by the pellicle again onto the pellicle, a second detector for detecting the light beam reflected again by the pellicle, and correction means for correcting an output signal from the first detector using an output signal from the second detector.

The foregoing and other objects, advantages and features of the present invention will become more apparent from the following description of the preferred embodiments taken in conjunction with the accompanying drawings.

BRIEF DESCRIPTION OF THE DRAWINGS

Like numerals have been used for like or corresponding elements throughout the views.

DESCRIPTION OF THE PREFERRED EMBODIMENTS

Figure 1:
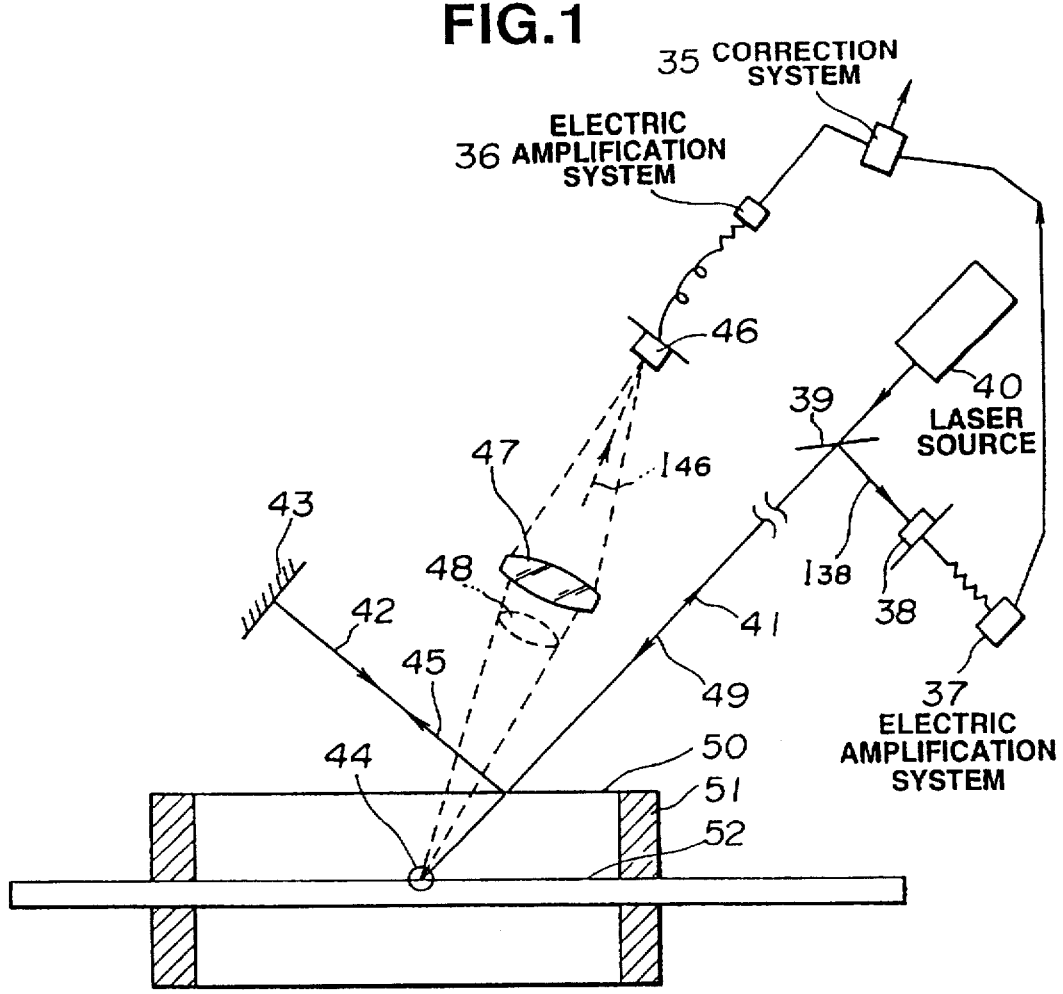
FIG. 1 is a schematic diagram illustrating a principal portion of an apparatus for detecting foreign matter on a substrate according to a first embodiment of the present invention.
Figure 2:
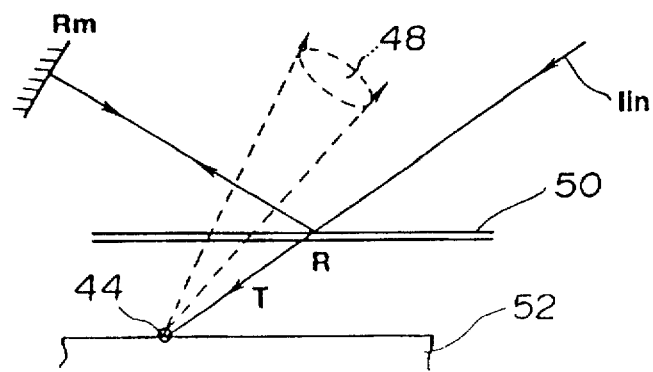
FIG. 2 is an enlarged view of a portion of FIG. 1.

FIG. 1 is a schematic diagram illustrating a principal portion of an apparatus for detecting foreign matter on a substrate according to a first embodiment of the present invention. FIG. 2 is an enlarged view of a portion of FIG. 1.

In FIG. 1, there are shown a laser light source 40, a beam splitter 39, and a laser beam 49. The laser beam 49 is emitted from the laser light source 40, and is projected toward a pellicle 50 via a scanning optical system comprising a polygonal mirror and the like (not shown). The scanning optical system scans the pellicle 50 and a photomask 52 in the x-axis direction, i.e., a direction perpendicular to the plane of FIG. 1, with the laser beam 49. A portion of the laser beam 49 which is projected onto foreign matter 44 on the photomask (a second surface) 52 via the pellicle (a first surface) 50 is scattered by the foreign matter 44. Scattered light 48 produced at that time is detected by a photodetector (a first detector) 46 via a condensing optical system 47.

An electric amplification system 36 amplifies an optical signal from the photodetector 46. A laser beam 45 obtained as a result of reflection of the laser beam 49 by the pellicle 50 is projected onto a mirror 43 substantially perpendicularly thereto, is reflected by the mirror 43, and returns along the original optical path. The light beam 45 is reflected again at substantially the same position on the pellicle 52 as in the first reflection to provide a light beam 41, which passes through the scanning optical system, is reflected by the beam splitter 39, and is incident upon a photodetector (a second detector) 38. An electric amplification system 37 amplifies a signal from the photodetector 38.

If the reflectivity of the pellicle 50 is represented by R, the transmittance of the pellicle 50 is represented by T, the reflectivity of the mirror 43 is represented by $R_m$ and the amount of the incident light beam 41 is represented by $I_{in}$, the amount $L_{44}$ of the laser beam projected onto the foreign matter 44 is $L_{44}=T \times I_{in}$. Since there is substantially no absorption in the pellicle 50, T=1−R.

In the present embodiment, the reflectivity R is obtained, and variations in the amount of the light beam projected onto the foreign matter 44 are corrected, based on the obtained reflectivity R. The original laser beam 49 is reflected by the pellicle 50 twice, and is reflected by the mirror 43 once. Accordingly, the intensity $I_{41}$ of the light beam 41 is expressed by $I_{41}=I_{in} \times R^2 \times R_m$.

Since the mirror 43 is fixed to the apparatus, the reflectivity $R_m$ of the mirror 43 has a constant value. Accordingly, if the transmittance of the beam splitter 39 is represented by $T_{39}$, the reflectivity of the beam splitter 39 is represented by $R_{39}$, the transmittance of the scanning optical system is represented by $T_{sc}$, and the original emission power of the laser 40 is represented by $L_0$, the amount $I_{38}$ of the light beam 41 incident upon the photodetector 38 is expressed by:

$$I_{38} = L_0 \times T_{39} \times T_{SC} \times R^2 \times R_m \times T_{SC} \times R_{39} \quad (1)$$
$$= L_0 \times T_{39} \times R_{39} \times T_{SC}^2 \times R_m \times R^2.$$

Since the values of $L_0$, $T_{39}$, $R_{39}$, $T_{sc}$ and $R_m$ are fixed values in the apparatus and therefore constant values, if the amount of light $I_{38}$ incident upon the photodetector 38 is known, the reflectivity R is expressed, from expression (1), by:

$$R = \sqrt{I_{38}/K}, \quad (2)$$

where $K = L_0 \times T_{39} \times R_{39} \times T_{sc}^2 \times R_m$. Accordingly, the intensity $L_{44}$ of the light beam projected onto the foreign matter 44 is corrected as:

$$L_{44} = (1-R) \times I_{in} = (1 - \sqrt{I_{38}/K})I_{in}. \quad (3)$$

That is, the light-amount coefficient changes by a factor $1 - \sqrt{I_{38}/K}$.

In FIG. 1, a correction system 35 performs such factor correction to obtain the exact size of the foreign matter 44. That is, if the amount of light $I_{38}$ is large, the transmission T of the pellicle 50 is small, and the amount of the light beam projected onto the foreign matter 44 is small. As a result, the amount of scattered light from the foreign matter 44 having the same size is small. Accordingly, in order to exactly determine that foreign matter has the same size from the amount of light $I_{46}$ incident upon the photodetector 46, the following approaches are, for example, taken.

(a) The slice level for a signal output from the electric amplification system 36 for determining the size of the foreign matter is changed in accordance with the amount of light $I_{38}$.

(b) The gain of the electric amplification system 36 is changed in accordance with the amount of light $I_{38}$.

Figure 12:
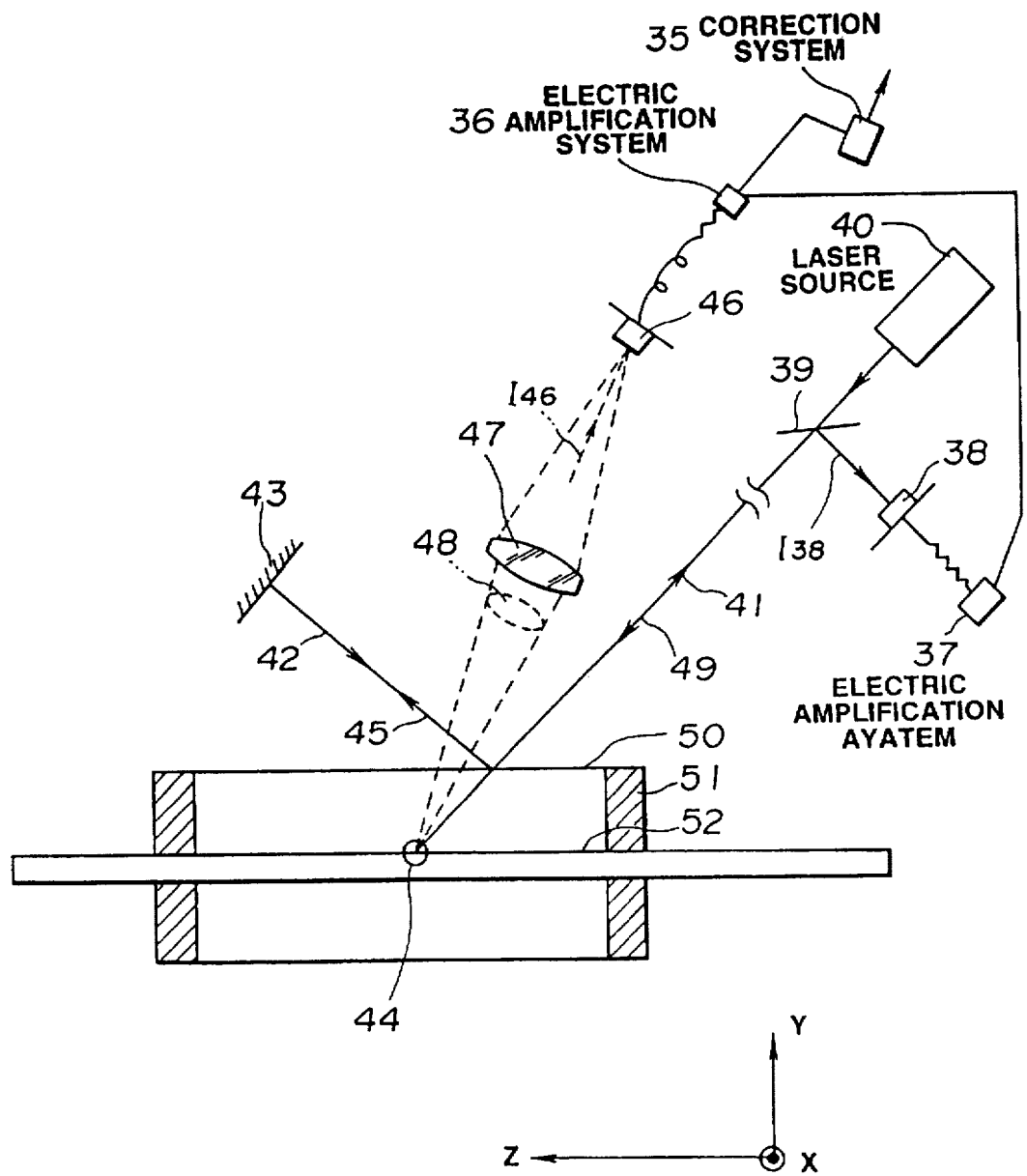
FIG. 12 is a schematic diagram illustrating a principal portion of an apparatus for detecting foreign matter on a substrate obtained by partially modifying the apparatus shown in FIG. 1.

In approach (a), as shown in FIG. 1, the correction system 35 has the function of changing the slice level based on the signal from the electric amplification system 37. In approach (b), as shown in FIG. 12, the amount of light $I_{38}$ is detected by the photodetector 38, and the gain of the electric amplification system 36 for amplifying the signal from the photodetector 46 is changed based on the signal output from the photodetector 38.

In the present embodiment, the amount of correction at that time is obtained from expression (2).

In FIG. 1, the scanning optical system performs the scanning of the laser beam 49 in the x-axis direction. The photomask (reticle) 52 is mounted on a stage (not shown), and is slowly moved in the z-axis direction. The entire surface of the photomask 52 is thereby scanned by the laser beam 49, and the scattered light 48 from foreign matter 44 present on the IC pattern on the photomask 52 is detected to determine the foreign matter.

Figure 3:
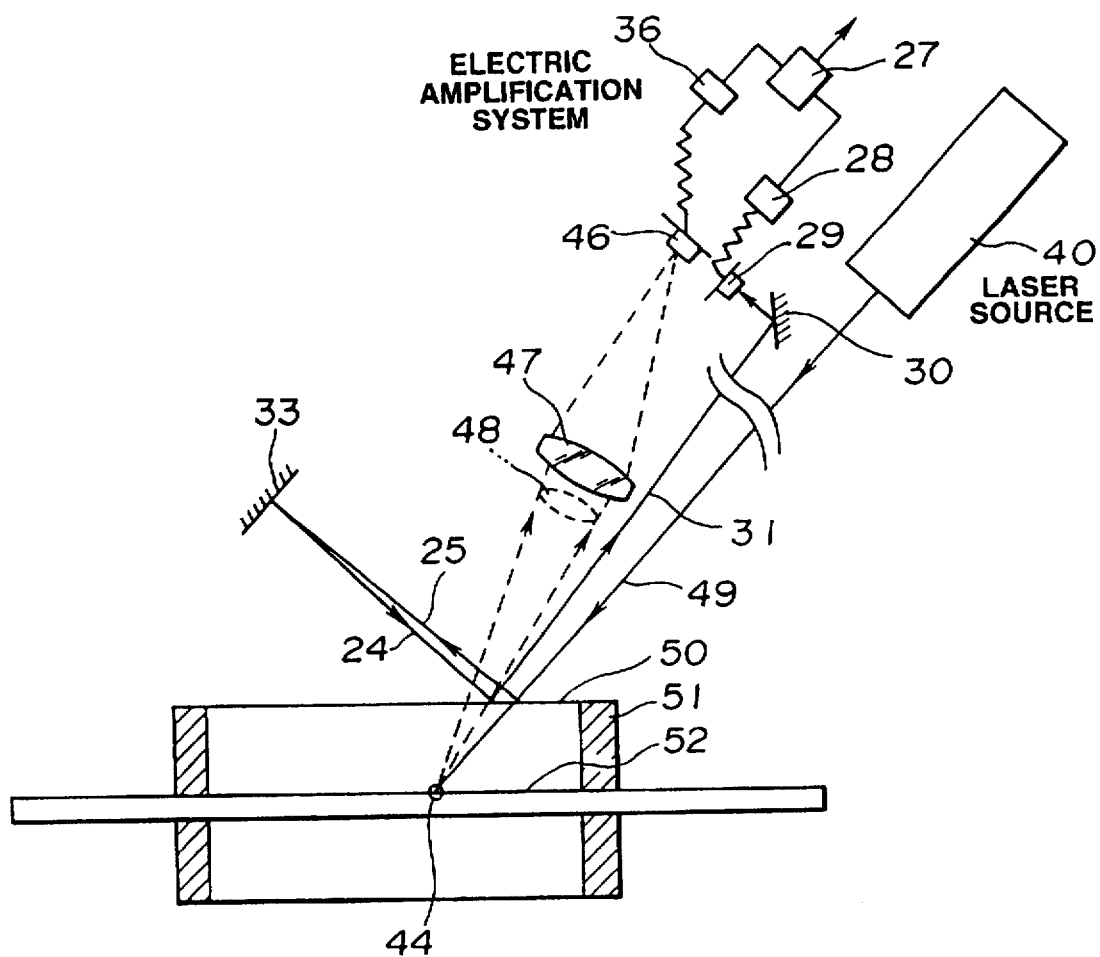
FIG. 3 is a schematic diagram illustrating a principal portion of an apparatus for detecting foreign matter on a substrate according to a second embodiment of the present invention.
Figure 4:
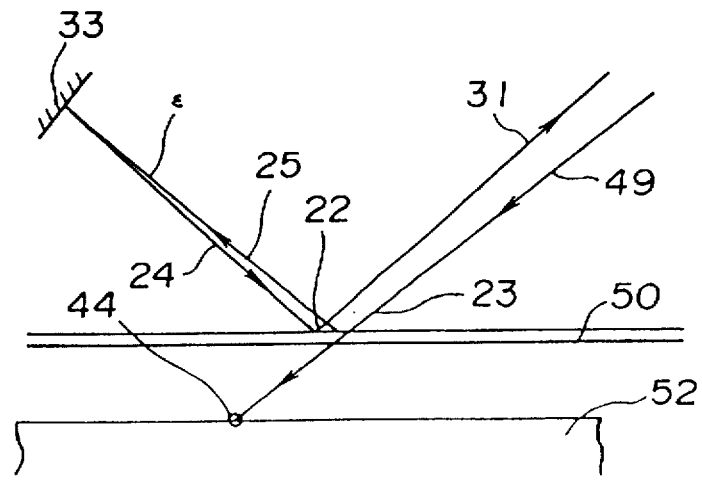
FIG. 4 is an enlarged view of a portion of FIG. 3.
Figure 5:
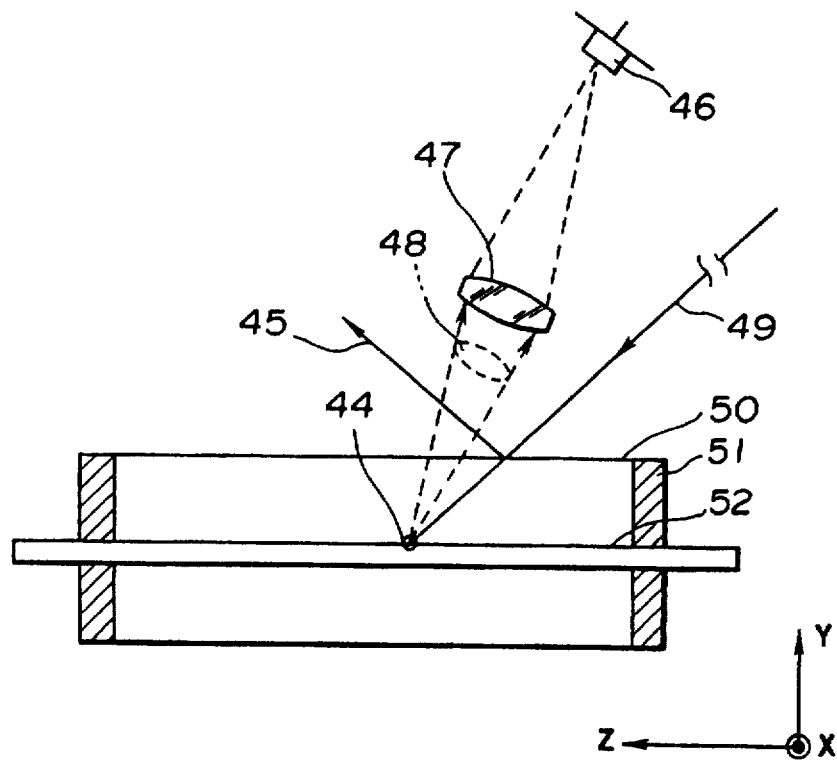
FIG. 5 is a schematic diagram illustrating a principal portion of a conventional foreign-matter inspection apparatus.
Figure 6:
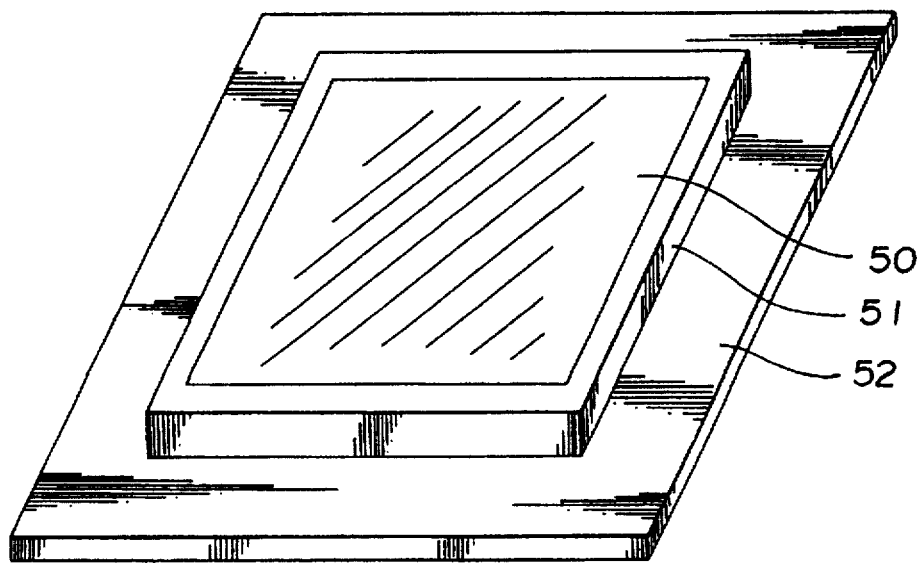
FIG. 6 is a diagram illustrating a conventional photomask on which a pellicle is mounted.

FIG. 3 is a schematic diagram illustrating a principal portion of an apparatus for detecting foreign matter on a substrate according to a second embodiment of the present invention. FIG. 4 is an enlarged view of a portion of FIG. 3.

This embodiment of the present invention differs from the first embodiment shown in FIG. 1 in that the inclination of a mirror 33 for returning a light beam reflected by a pellicle 50 is adjusted, so that the incident angle of a light beam 25 onto the mirror 33 produced after being reflected by the pellicle 50 is not 0 (i.e., perpendicular to the mirror 33), but has a small value. The optical path of a light beam 24 produced after being reflected by the mirror 33 differs from that of the light beam 25, so that it is unnecessary to use the beam splitter 39 shown in FIG. 1.

The beam splitter 39 shown in FIG. 1 also can be omitted in the configuration shown in FIG. 12.

As described above, the present embodiment has a feature of omitting the beam splitter 39, so that the amount of the light beam from the laser 40 can be efficiently utilized without being reduced by the beam splitter 39.

As shown in detail in FIG. 4, the angle ϵ made by the light beam 25 and the light beam 24 is set within a range to satisfy the following two conditions.

(i) The position 23 on the pellicle 50 where the light beam 49 is projected is not separated too much from the position 22 where the light beam 24 is projected.

(ii) The incident angle of the light beam 49 onto the pellicle 50 does not differ too much from the incident angle of the returning light beam 24 onto the pellicle 50.

The condition (i) is set because in general, variations in the thickness of the pellicle 50 are present at some portions, and the distance between the points 22 and 23 must be sufficiently shorter than the period of the occurrence of the variations.

In general, variations of at most one period occur in the thickness of the pellicle 50 having a size of 5 inches. Hence, a distance between the points 22 and 23 of less than ten and a few millimeters will cause no problem, because such a distance can be considered to be within a region of substantially the same thickness.

Figure 7:
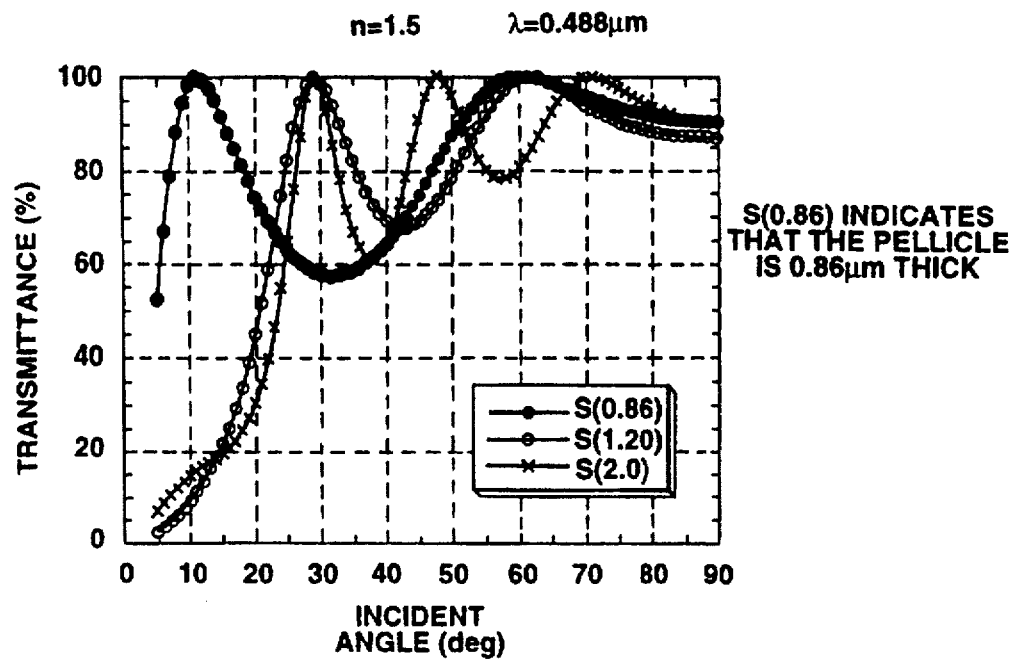
FIG. 7 is a diagram illustrating the relationship between the thickness of a pellicle and transmittance for S-polarized light.
Figure 8:
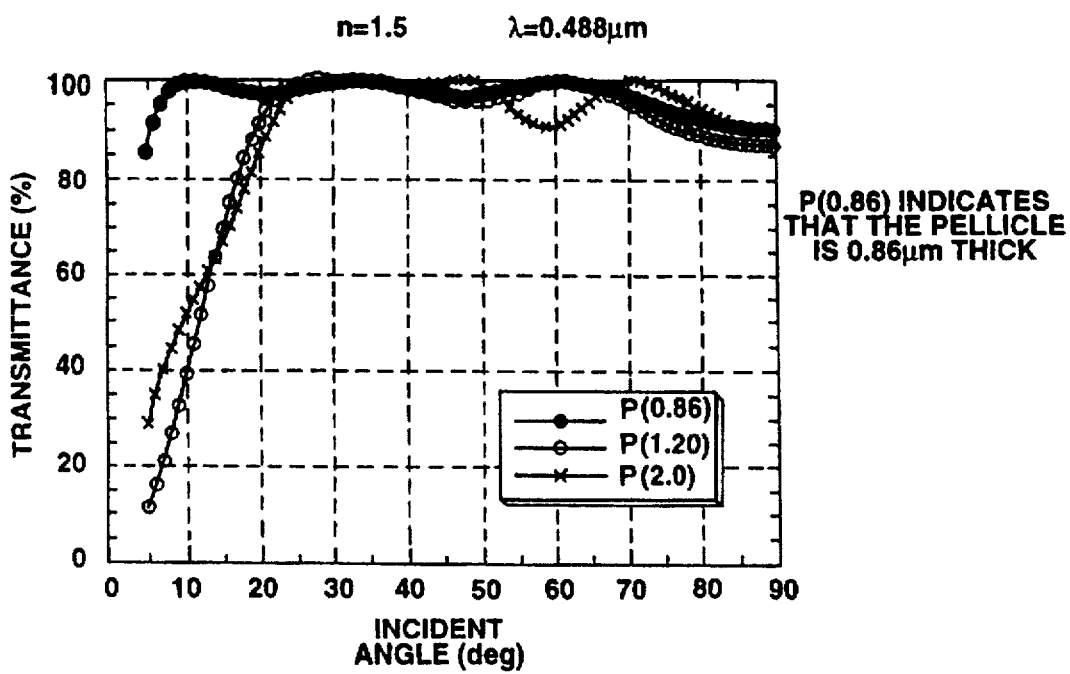
FIG. 8 is a diagram illustrating the relationship between the thickness of a pellicle and transmittance for P-polarized light.

The condition (ii) is set because the reflectivity and the transmittance generally change when the incident angle changes. However, such a phenomenon is a matter of degree. For example, as shown in FIG. 7, in the case of incidence of S-polarized light, the transmittance changes with the incident angle and the pellicle's thickness. In the case of incidence of P-polarized light, the transmittance changes as shown in FIG. 8. As can be understood from FIGS. 7 and 8, the transmittance changes only about 2–3% when the incident angle changes about 2°–3°, provided that the incident angle is not too small, i.e., for example, the incident angle is equal to or greater than 25°. Hence, in practice, no problem will arise. Accordingly, in the present embodiment, the angle ϵ is set to be equal to or less than 2°–3°.

In the above-described first and second embodiments, the case, in which incident light is projected and scattered light is sensed within the same surface (the plane of each of FIGS. 1 through 4), has been shown. However, the present invention is not limited to such a case.

Although in the case of FIG. 1 the scattered light is received in the yz plane, the scattered light may be sensed in a lateral direction by a photosensing system disposed at some position in the x-axis direction. The scattered light may also be sensed at a position inclined with respect to a side opposite to the light-projecting system (in the positive z-axis direction) instead of being sensed at a position inclined with respect to the side of the light-projection system.

In the present invention, there is no limitation with respect to variations in the light-projecting system and the light-sensing system. The incident light onto the pellicle may comprise any polarized light other than S-polarized light or P-polarized light, such as circularly-polarized light, for example.

In the above-described embodiments, the intensity of the scattered light is directly detected. However, a method of detecting foreign matter on a substrate by processing an interference signal between scattered light from the foreign matter and reference light generated in the apparatus may also be adopted, and a monitoring function may be provided for reflected light from the pellicle after passing through the pellicle and being projected onto the foreign matter.

Figure 9:
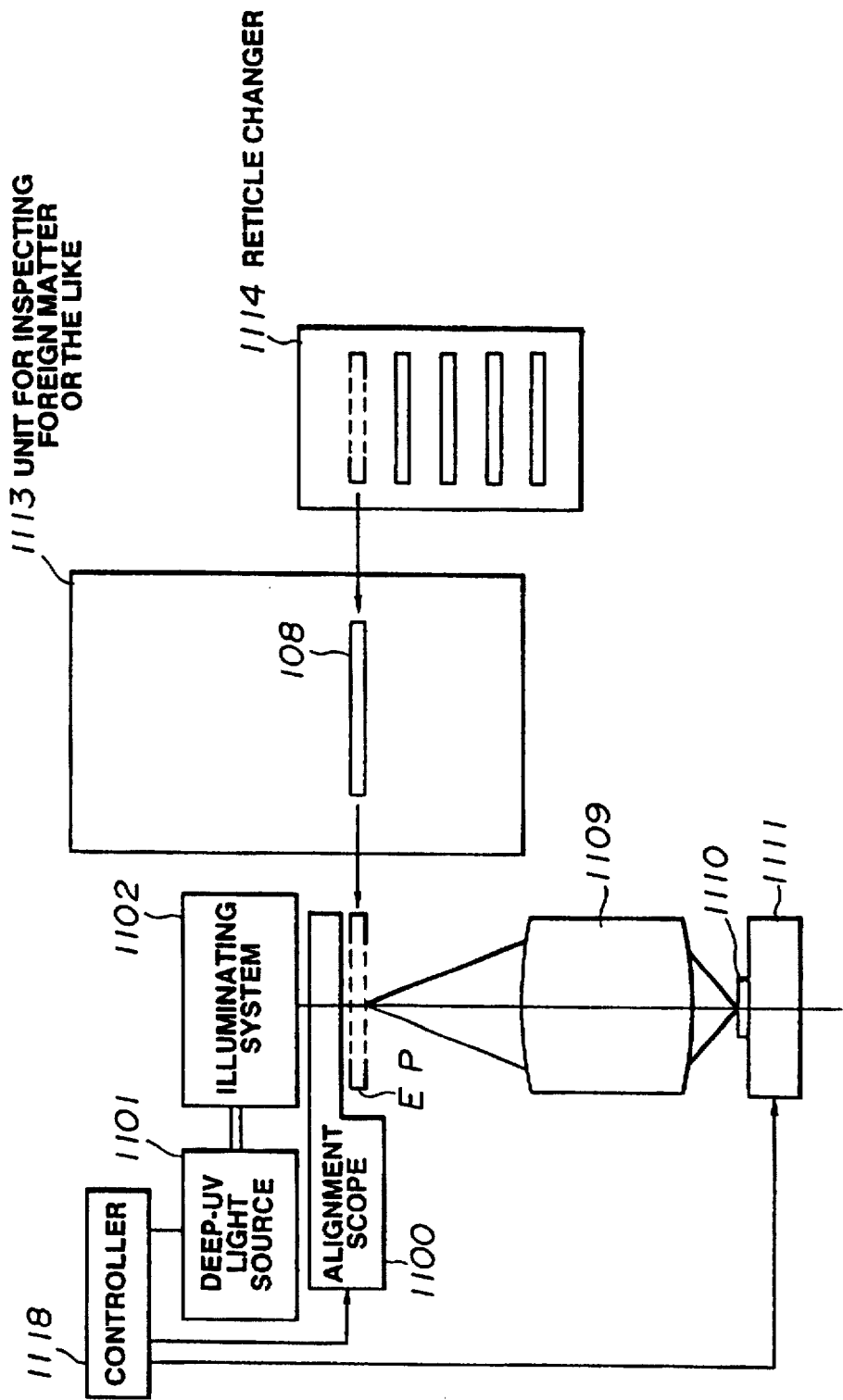
FIG. 9 is a schematic diagram illustrating a principal portion of a semiconductor-device manufacturing apparatus incorporating an apparatus for detecting foreign matter on a substrate according to a third embodiment of the present invention.

FIG. 9 is a schematic diagram illustrating the configuration of a third embodiment, in which an apparatus for detecting foreign matter on a substrate of the present invention is applied to a semiconductor-device manufacturing apparatus. In the present embodiment, the entire detection apparatus is incorporated within the semiconductor-device manufacturing apparatus.

In FIG. 9, reference numeral 1101 represents a deep-UV light source, such as an excimer laser. An illuminating system 1102 illuminates the entire region to be inspected on a reticle 108 from above simultaneously (at one time) with a predetermined NA (numerical aperture). An ultrahigh-resolution lens system (or mirror system) 1109 transfers a reticle pattern onto a wafer 1110. In a printing operation, the wafer 1110 is sequentially shifted by one shot in accordance with the stepwise movement of a wafer moving stage 1111, whereby the reticle pattern is exposed onto the wafer 1110.

An alignment optical system 1100 aligns the wafer 1110 with the reticle 108 before exposure, and includes at least one microscope system for observing the reticle. A reticle changer 1114 accommodates a plurality of reticles waiting for exposure. A unit 1113 for detecting foreign matter or the like includes all the components included in one of the first and second embodiments. The unit 1113 inspects foreign matter on the reticle 108 before the reticle 108 is set at an exposure position (EP shown in FIG. 9) after it has been taken out of the reticle changer 1114.

A controller 1118 controls the sequence of alignment exposure and the stepwise movement of the wafer, which are the basic operations of the stepper.

Next, a description will be provided of a semiconductor-device manufacturing method utilizing the above-described exposure apparatus.

Figure 10:
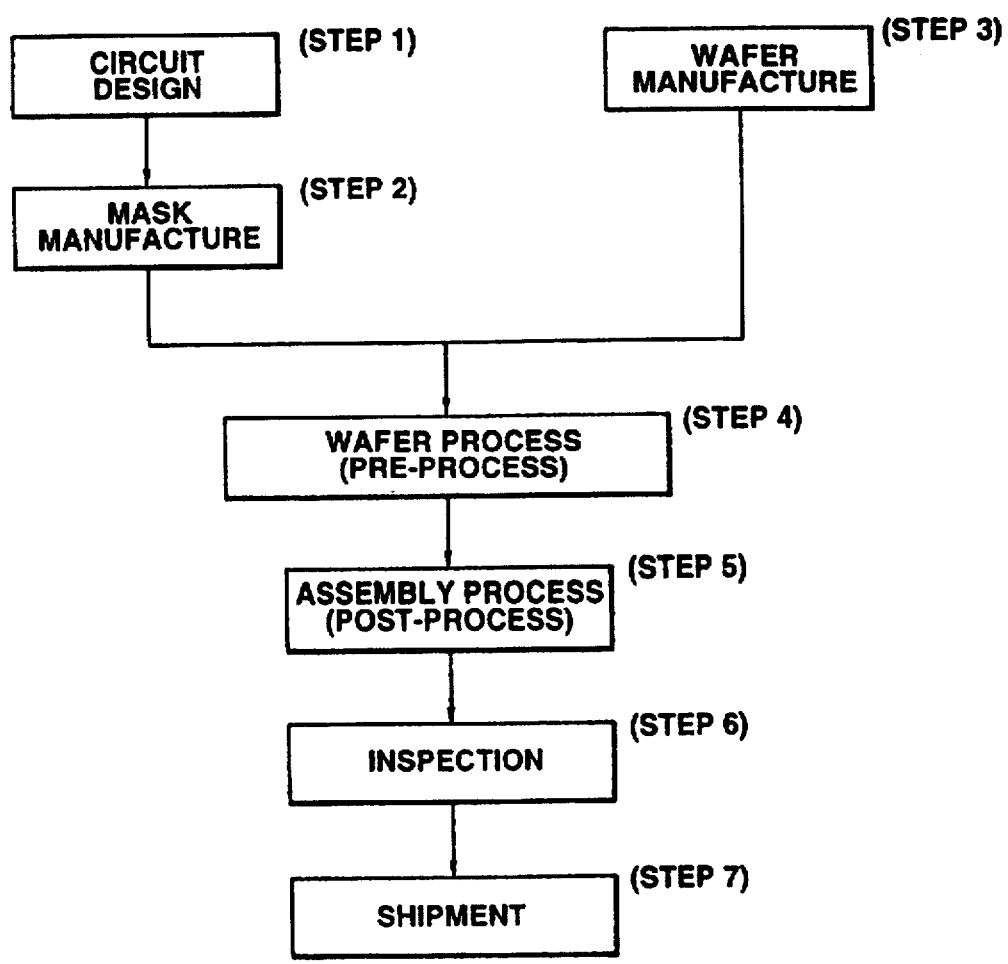
FIGS. 10 and 11 are flowcharts illustrating a semiconductor-device manufacturing method according to the present invention.

FIG. 10 is a flowchart for the manufacture of semiconductor devices (semiconductor chips of IC's, LSI's (large-scale integrated circuits) or the like, liquid-crystal panels, CCD's (charge-coupled devices), or the like.

In step 1 (circuit design), circuit design of semiconductor devices is performed. In step 2 (mask manufacture), masks on which designed circuit patterns are formed are manufactured.

In step 3 (wafer manufacture), wafers are manufactured using a material, such as silicon or the like. Step 4 (wafer process) is called a preprocess, in which actual circuits are formed on the wafers by means of photolithography using the above-described masks and wafers.

The next step 5 (assembly process) is called a postprocess, which manufactures semiconductor chips using the wafers manufactured in step 4, and includes an assembling process (dicing and bonding), a packaging process (chip encapsulation), and the like.

In step 6 (inspection), inspection operations, such as operation-confirming tests, durability tests, and the like of the semiconductor devices manufactured in step 5, are performed. The manufacture of semiconductor devices is completed after passing through the above-described processes, and the manufactured devices are shipped (step 7).

Figure 11:
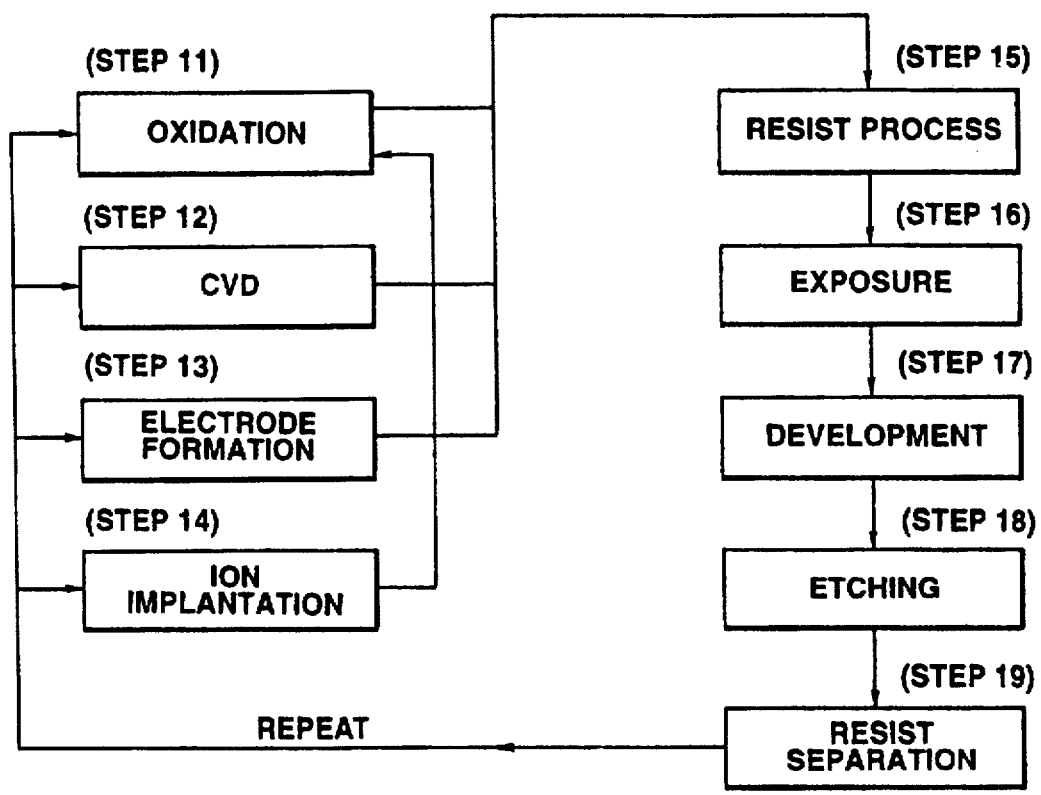

FIG. 11 is the detailed flowchart of the above-described wafer process shown in step 4 of FIG. 10. First, in step 11 (oxidation), the surface of the wafer is oxidized. In step 12 (CVD), an insulating film is formed on the surface of the wafer.

In step 13 (electrode formation), electrodes are formed on the surface of the wafer by vacuum deposition. In step 14 (ion implantation), ions are implanted into the wafer. In step 15 (resist process), a photosensitive material is coated on the wafer. In step 16 (exposure), the circuit pattern on the mask is exposed and printed on the wafer by the above-described exposure apparatus.

In step 17 (development), the exposed wafer is developed. In step 18 (etching), portions other than the developed resist image are etched off. In step 19 (resist separation), the resist, which becomes unnecessary after the completion of the etching, is removed. By repeating these steps, a final circuit pattern made of multiple patterns is formed on the wafer.

By using the manufacturing method of the present embodiment, it is possible to easily manufacture semiconductor devices with a high degree of integration.

The individual components shown in outline or designated by blocks in the drawings are all well known in the foreign-matter inspection apparatus and exposure apparatus arts and their specific construction and operation are not critical to the operation or the best mode for carrying out the invention.

While the present invention has been described with respect to what is presently considered to be the preferred embodiments, it is to be understood that the invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An apparatus for detecting foreign matter on a substrate, said apparatus comprising:

optical means for projecting a monochromatic light beam through a first surface onto a second surface;

a first detector for detecting scattered light from foreign matter on the second surface and for producing a first detection signal;

first amplifying means for receiving and amplifying the first detection signal to produce a first amplified detection signal;

a second detector for detecting information relating to one of the reflectivity and the transmittance of the first surface by detecting a light beam reflected by the first surface and for producing a second detection signal;

second amplifying means for receiving and amplifying the second detection signal to produce a second amplified detection signal; and correction means for receiving the first and second amplified detection signals and for changing one of (i) a slice level for the first amplified detection signal and (ii) again of said first amplifying means.

2. An apparatus according to claim 1, wherein the first surface comprises a pellicle surface, and wherein the second surface comprises a mask-pattern surface.

3. An apparatus according to claim 1, wherein the light beam comprises a laser beam having a predetermined polarization state.

4. An apparatus for detecting foreign matter on a substrate, said apparatus comprising:

optical means for projecting a monochromatic light beam through a first surface onto a second surface;

a first detector for detecting scattered light from foreign matter on the second surface and for producing a first detection signal;

first amplifying means for receiving and amplifying the first detection signal to produce a first amplified detection signal;

means for projecting the light beam reflected by the first surface again onto the first surface;

a second detector for detecting the light beam reflected again by the first surface and for producing a second detection signal;

second amplifying means for receiving and amplifying the second detection signal to produce a second amplified detection signal; and correction means for receiving the first and second amplified detection signals and for changing one of (i) a slice level for the first detection signal and (ii) a gain of the first amplifying means.

5. An apparatus according to claim 4, wherein the first surface comprises a pellicle surface, and wherein the second surface comprises a mask-pattern surface.

6. An apparatus according to claim 4, wherein the light beam comprises a laser beam having a predetermined polarization state.

7. An exposure apparatus, comprising:

exposure means for performing exposure using a mask, which includes a pellicle and a pattern surface; and an inspection apparatus for inspecting foreign matter on the mask, said inspection apparatus comprising:

optical means for projecting a monochromatic light beam through a first surface onto a second surface;

a first detector for detecting scattered light from foreign matter on the second surface and for producing a first detection signal;

first amplifying means for receiving and amplifying the first detection signal to produce a first amplified detection signal;

a second detector for detecting information relating to one of the reflectivity and the transmittance of the pellicle by detecting the light beam reflected by the pellicle and for producing a second detection signal;

second amplifying means for receiving and amplifying the second detection signal to produce a second amplified detection signal; and correction means for receiving the first and second amplified detection signals and for changing one of (i) a slice level for the first detection signal and (ii) a gain of the first amplifying means.

8. An apparatus according to claim 7, wherein the light beam projected by said optical means comprises a laser beam having a predetermined polarization state.

9. An exposure apparatus, comprising:

exposure means for performing exposure using a mask, which includes a pellicle and a pattern surface; and an inspection apparatus for inspecting foreign matter on the mask, said inspection apparatus comprising:

optical means for projecting a monochromatic light beam onto the pellicle and the pattern surface;

a first detector for detecting scattered light from foreign matter on the pattern surface and for producing a first detection signal;

first amplifying means for receiving and amplifying the first detection signal to produce a first amplified detection signal;

means for projecting the light beam reflected by the pellicle again onto the pellicle;

a second detector for detecting the light beam reflected again by the pellicle and for producing a second detection signal;

second amplifying means for receiving and amplifying the second detection signal to produce a second amplified detection signal; and correction means for receiving the first and second amplified detection signals and for changing one of (i) a slice level for the first detection signal and (ii) a gain of the first amplifying means.

10. An apparatus according to claim 9, wherein the light beam projected by said optical means comprises a laser beam having a predetermined polarization state.

* * * * *

UNITED STATES PATENT AND TRADEMARK OFFICE
CERTIFICATE OF CORRECTION

PATENT NO. : 5,742,386

DATED : April 21, 1998

INVENTOR(S) : NORIYUKI NOSE, ET AL.   Page 1 of 3

It is certified that error appears in the above-identified patent and that said Letters Patent is hereby corrected as shown below:

ON THE COVER PAGE

After item [58], insert

--[56]       References Cited

U.S. PATENT DOCUMENTS

| | | | |
|---|---|---|---|
| 3,734,626 | 5/1973 | Roberts et al. | 356/120 |
| 4,724,481 | 2/1981 | Nishioka | 358/106 |
| 4,866,287 | 9/1989 | Weber | 250/571 |
| 4,999,511 | 3/1991 | Kohno | 250/572 |
| 5,017,798 | 5/1991 | Murakami et al. | 250/572 |
| 5,072,128 | 12/1991 | Hayano et al. | 250/572 |
| 5,106,194 | 4/1992 | Kuchel | 356/360 |
| 5,148,037 | 9/1992 | Suda et al. | 250/548 |
| 5,200,800 | 4/1993 | Suda et al. | 356/401 |
| 5,270,794 | 12/1993 | Tsuji et al. | 356/371 |
| 5,291,023 | 3/1994 | Hasegawa et al. | 250/548 |
| 5,333,050 | 7/1994 | Nose et al. | 356/356 --. |

UNITED STATES PATENT AND TRADEMARK OFFICE
CERTIFICATE OF CORRECTION

PATENT NO. : 5,742,386

DATED : April 21, 1998

INVENTOR(S) : NORIYUKI NOSE, ET AL.

It is certified that error appears in the above-identified patent and that said Letters Patent is hereby corrected as shown below:

IN THE DRAWINGS

In sheet 8, FIGURE 12:
    "AYATEM" should read --SYSTEM--.

IN THE DISCLOSURE

COLUMN 1:

line 46, "tranparent" should read --transparent--.

COLUMN 2:

line 5, "1.0 $\mu$m 2.0 $\mu$m," should read --1.0 $\mu$m-2.0 $\mu$m--.

UNITED STATES PATENT AND TRADEMARK OFFICE
CERTIFICATE OF CORRECTION

PATENT NO. : 5,742,386

DATED : April 21, 1998

INVENTOR(S): NORIYUKI NOSE, ET AL.

It is certified that error appears in the above-identified patent and that said Letters Patent is hereby corrected as shown below:

COLUMN 6:

line 39, "FIG. 8. As" should read --FIG. 8.  ¶As--.

COLUMN 8:

line 53, "again" should read --a gain--.

Signed and Sealed this

Fifteenth Day of December, 1998

*Attest:*

BRUCE LEHMAN

*Attesting Officer*  Commissioner of Patents and Trademarks